(12) United States Patent
Murray et al.

(10) Patent No.: US 11,547,833 B2
(45) Date of Patent: *Jan. 10, 2023

(54) COMPACT URINARY CATHETERS AND METHODS FOR MAKING THE SAME

(71) Applicant: Hollister Incorporated, Libertyville, IL (US)

(72) Inventors: Michael G. Murray, Ballina (IE); Daniel E. O'Brien, Calry (IE); David Hannon, Ballina (IE); Adam J. Foley, Swords (IE); Scott Allen, Frederiksberg (DK)

(73) Assignee: Hollister Incorporated, Libertyville, IL (US)

( * ) Notice: Subject to any disclaimer, the term of this patent is extended or adjusted under 35 U.S.C. 154(b) by 1076 days.

This patent is subject to a terminal disclaimer.

(21) Appl. No.: 16/197,009

(22) Filed: Nov. 20, 2018

(65) Prior Publication Data
US 2019/0083746 A1 Mar. 21, 2019

Related U.S. Application Data

(62) Division of application No. 14/775,533, filed as application No. PCT/US2013/031643 on Mar. 14, 2013, now Pat. No. 10,166,366.

(51) Int. Cl.
*A61M 25/01* (2006.01)
*A61F 5/453* (2006.01)
(Continued)

(52) U.S. Cl.
CPC ............. *A61M 25/01* (2013.01); *A61F 5/453* (2013.01); *A61F 5/455* (2013.01); *A61M 25/002* (2013.01);
(Continued)

(58) Field of Classification Search
CPC ........ A61F 5/453; A61F 5/455; A61F 5/4553; A61F 5/4556; A61M 25/01;
(Continued)

(56) References Cited

U.S. PATENT DOCUMENTS 4,205,819 A 6/1980 Soika
4,349,022 A 9/1982 Ishikawa
(Continued)

FOREIGN PATENT DOCUMENTS

GB 2460660 A 12/2009
WO 94/26342 A1 11/1994
(Continued)

OTHER PUBLICATIONS

International Search Report, for International Application No. PCT/US2013/031643, dated Dec. 16, 2013.
(Continued)

*Primary Examiner* — Philip R Wiest
(74) *Attorney, Agent, or Firm* — Cook Alex Ltd.

(57) ABSTRACT

A compact catheter assembly and methods of making such a catheter are disclosed. The catheter assembly incudes a receiver and a catheter sub-assembly. The catheter sub-assembly includes a gripping member and a catheter tube carried by the gripping member.

37 Claims, 10 Drawing Sheets

(51) Int. Cl.
*A61F 5/455* (2006.01)
*A61M 25/00* (2006.01)

(52) U.S. Cl.
CPC .... *A61M 25/0017* (2013.01); *A61M 25/0074* (2013.01); *A61M 25/0111* (2013.01); *A61M 2025/0175* (2013.01); *A61M 2210/1085* (2013.01)

(58) Field of Classification Search
CPC ............ A61M 25/0017; A61M 25/002; A61M 25/0074; A61M 25/0111; A61M 2025/0175; A61M 2210/1085
See application file for complete search history.

(56) References Cited

U.S. PATENT DOCUMENTS

| | | | |
|---|---|---|---|
| 4,615,692 A | 10/1986 | Giacalone et al. | |
| 4,767,409 A | 8/1988 | Brooks | |
| 5,653,700 A * | 8/1997 | Byrne | A61M 25/01 604/328 |
| D747,184 S | 1/2016 | Murray et al. | |
| 9,707,375 B2 | 7/2017 | Conway | |
| 10,166,366 B2 * | 1/2019 | Murray | A61M 25/002 |
| 2004/0158231 A1 * | 8/2004 | Tanghoj | A61M 25/0067 604/544 |
| 2007/0066963 A1 * | 3/2007 | Tanghoj | A61M 25/0017 604/523 |
| 2008/0172042 A1 | 7/2008 | House | |
| 2008/0182042 A1 * | 7/2008 | McCarthy | B42D 15/00 83/56 |
| 2009/0054876 A1 | 2/2009 | Borodulin et al. | |
| 2010/0087801 A1 * | 4/2010 | Torstensen | A61M 25/002 206/364 |
| 2011/0114520 A1 * | 5/2011 | Matthison-Hansen | A61M 25/0111 206/364 |
| 2012/0168324 A1 * | 7/2012 | Carleo | A61M 25/002 206/210 |
| 2012/0203142 A1 | 8/2012 | Bedell | |

FOREIGN PATENT DOCUMENTS

| | | |
|---|---|---|
| WO | 96/41653 A1 | 12/1996 |
| WO | 99/45997 A1 | 9/1999 |
| WO | WO 2004/089454 A1 | 10/2004 |
| WO | WO 2008/009590 A1 | 1/2008 |
| WO | WO 2010/006620 A1 | 1/2010 |
| WO | WO 2011/019359 A1 | 2/2011 |
| WO | 2012/134804 A1 | 10/2012 |

OTHER PUBLICATIONS

Written Opinion of the International Searching Authority for International Application No. PCT/US2013/031643, dated Dec. 16, 2013.
International Preliminary Report on Patentability of the International Searching Authority for International Application No. PCT/US2013/031643, dated Sep. 15, 2015.
Notice of Opposition against EP2968833 dated Feb. 25, 2022.
Coloplast SpeediCath Product Monograph published Mar. 1, 2010.

* cited by examiner

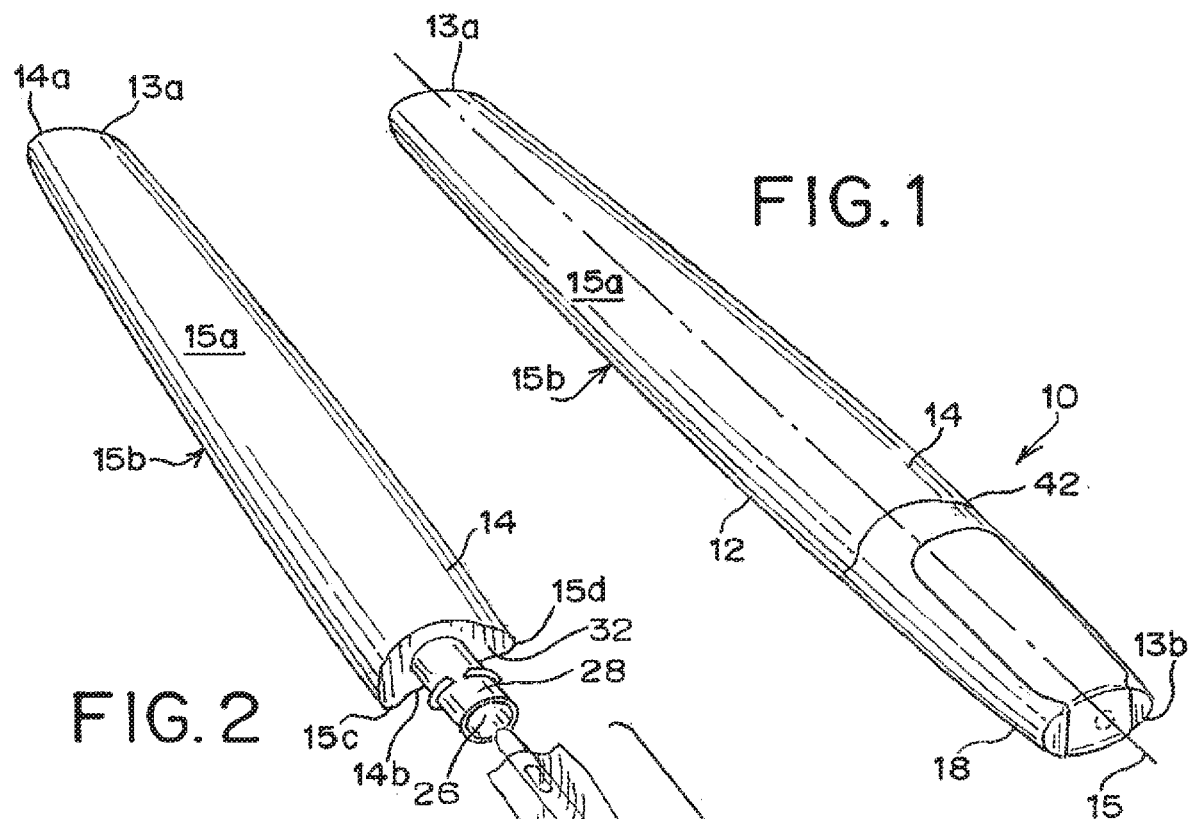
FIG. 1
FIG. 2
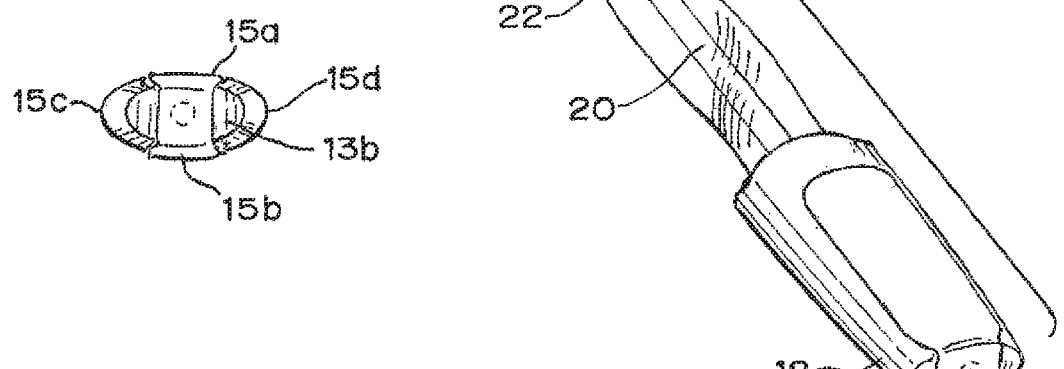
FIG. 3
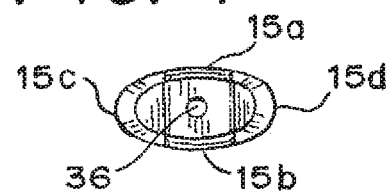
FIG. 4

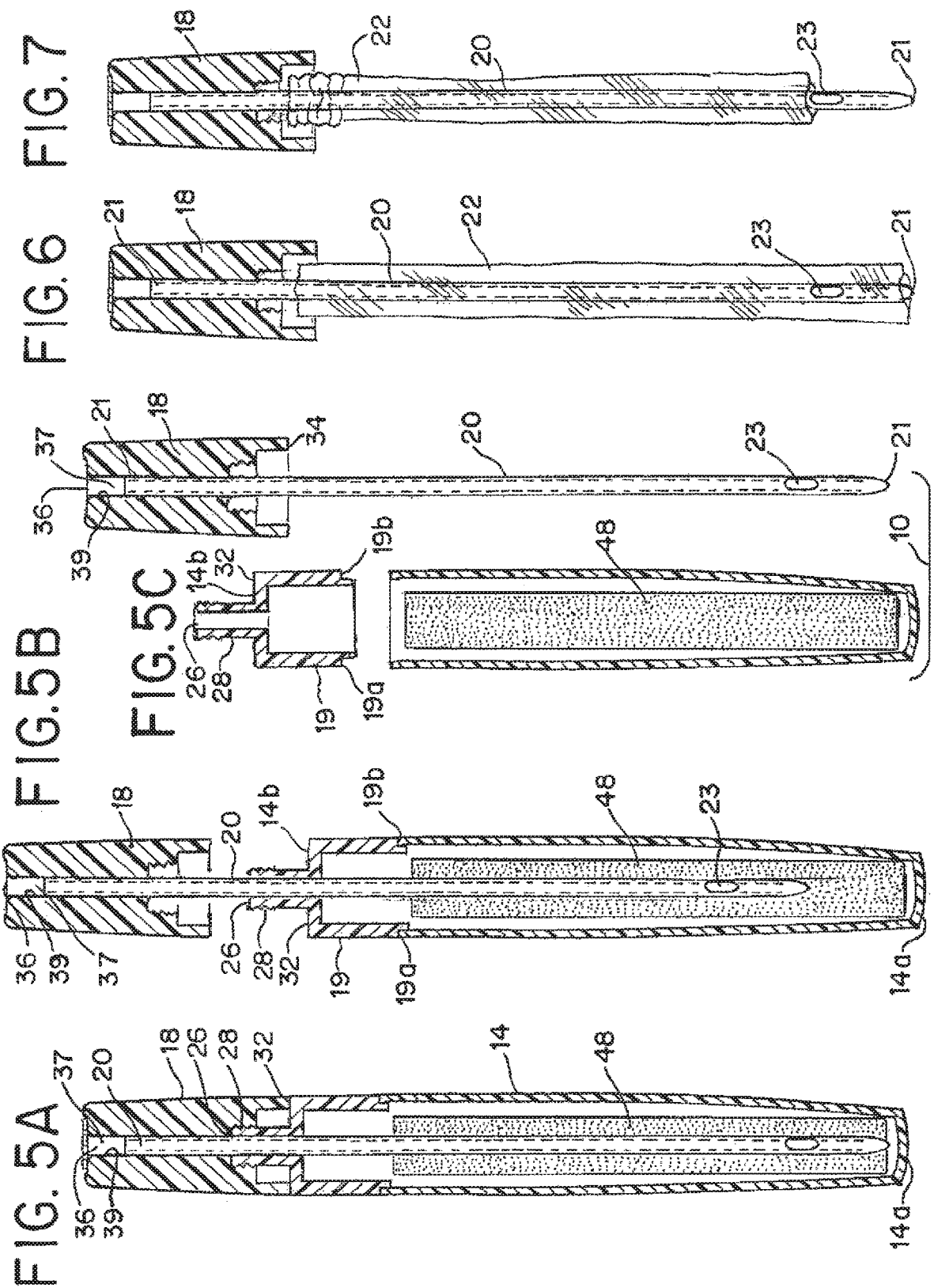

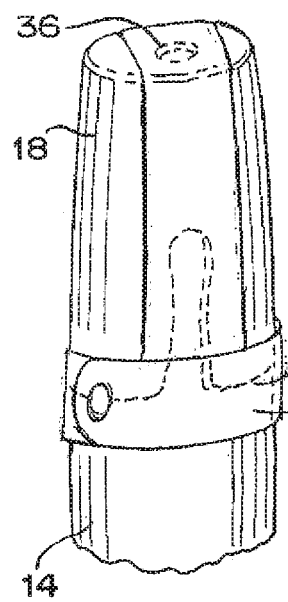
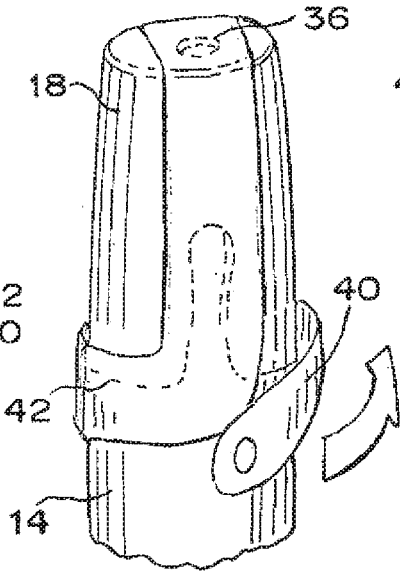
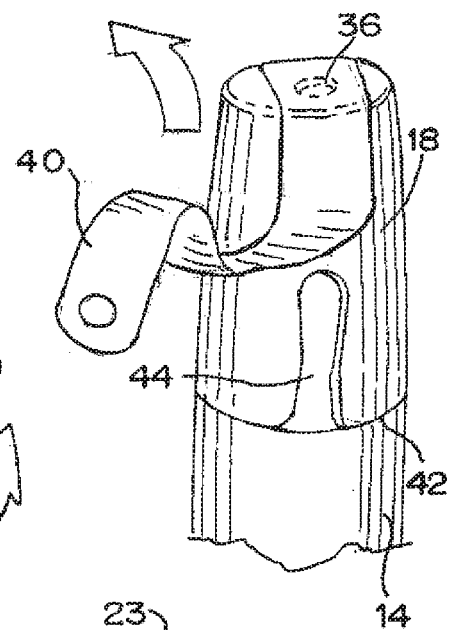
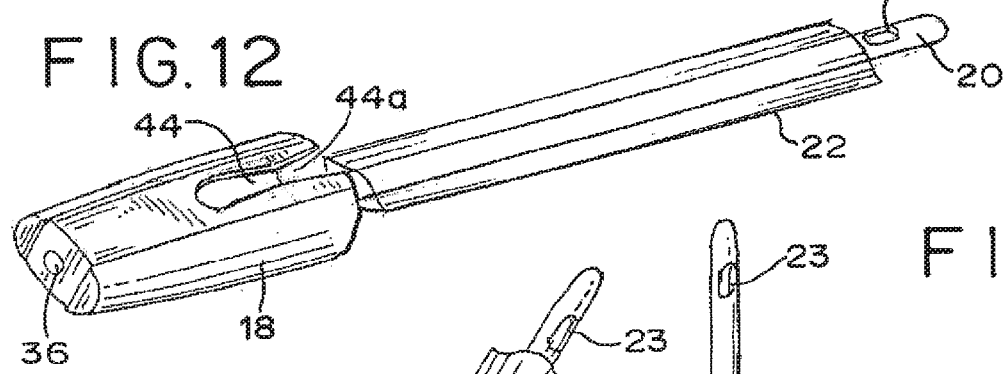
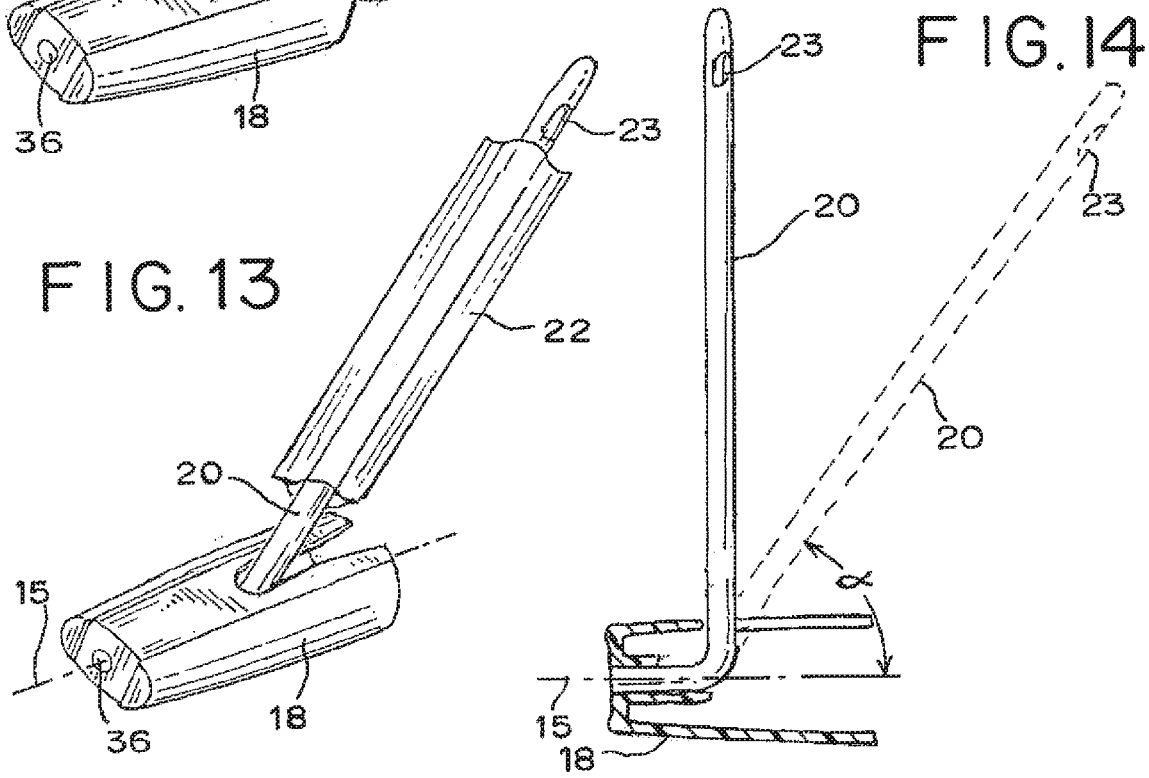
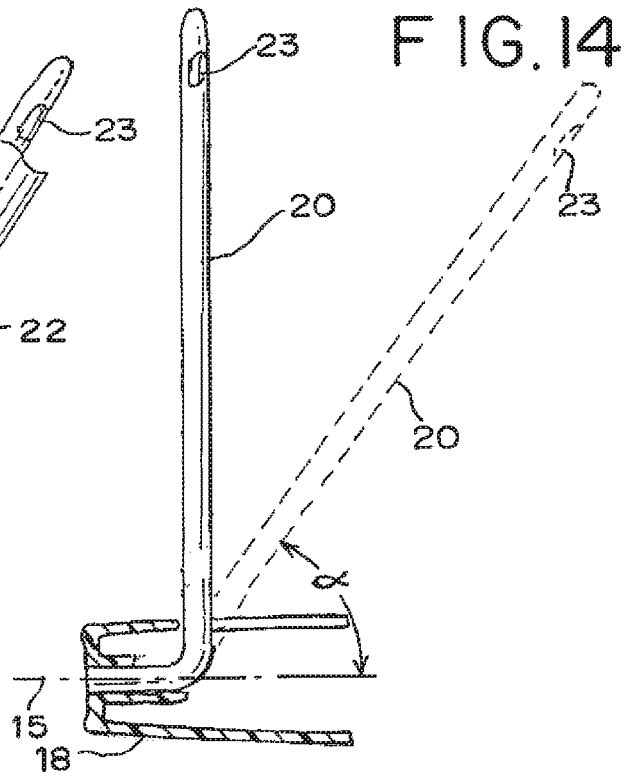

FIG.15
FIG.16
FIG.17
FIG.18
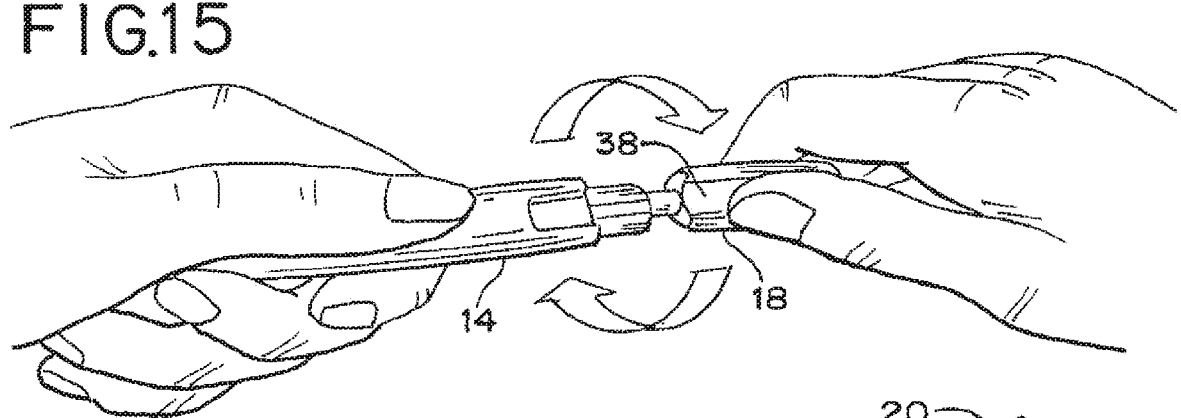
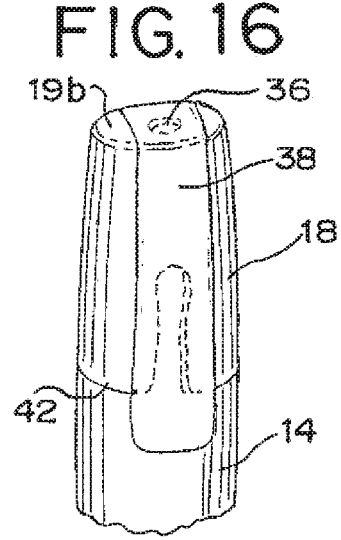
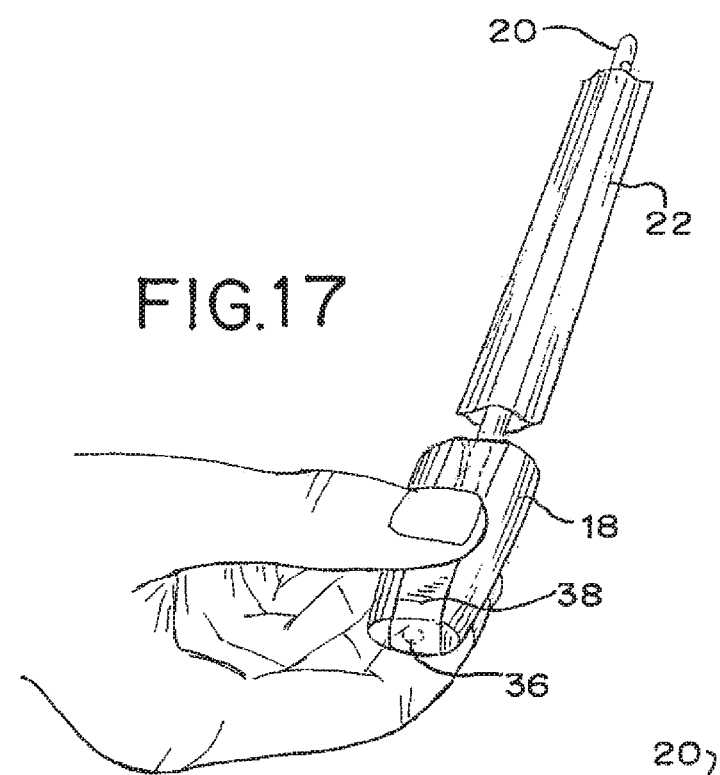
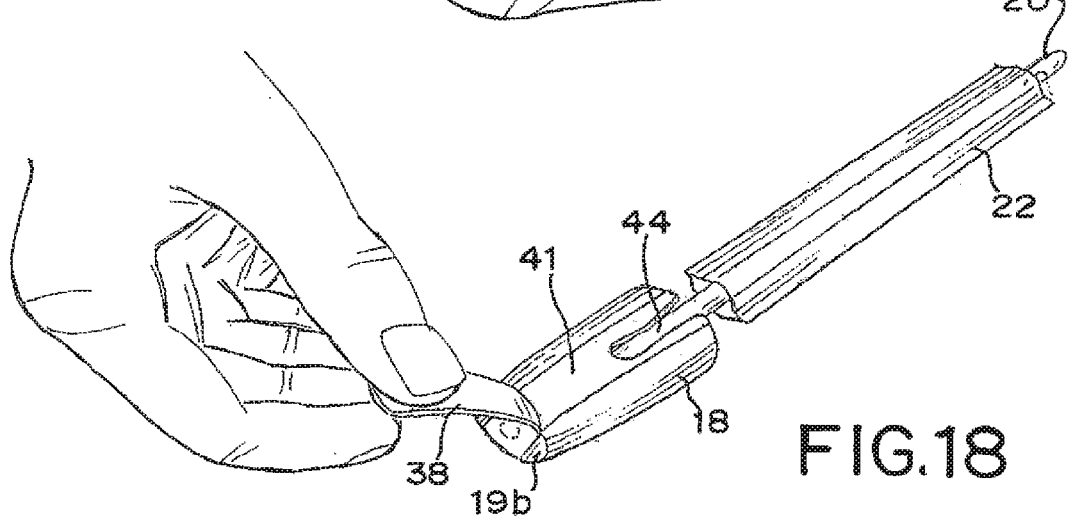

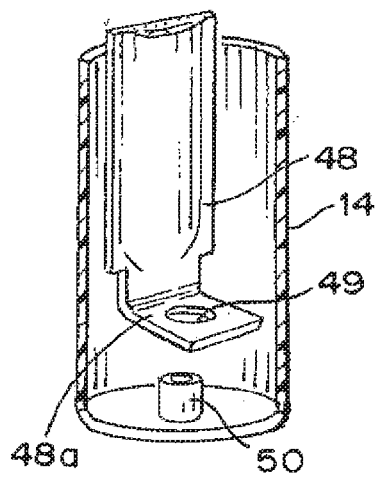
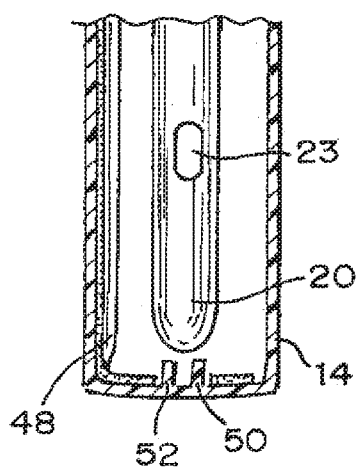
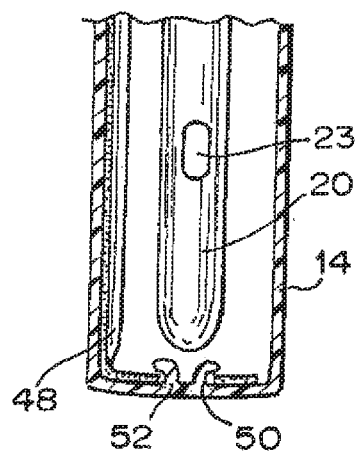
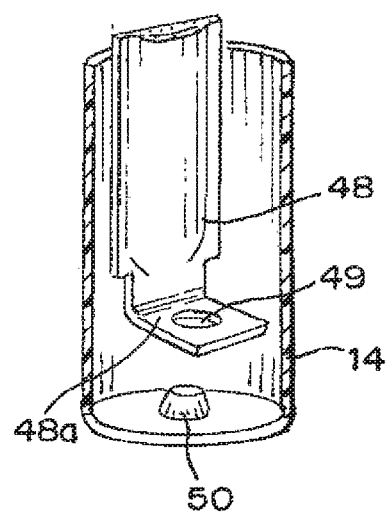
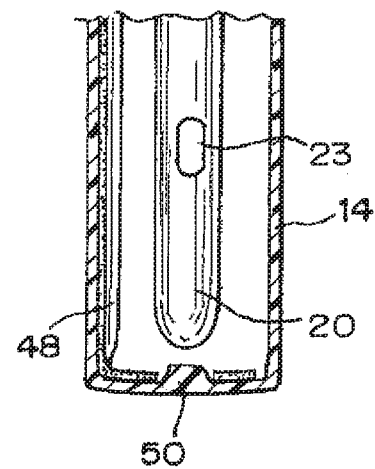
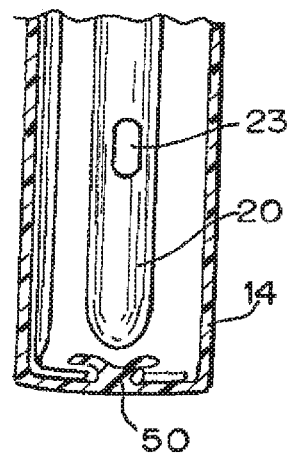
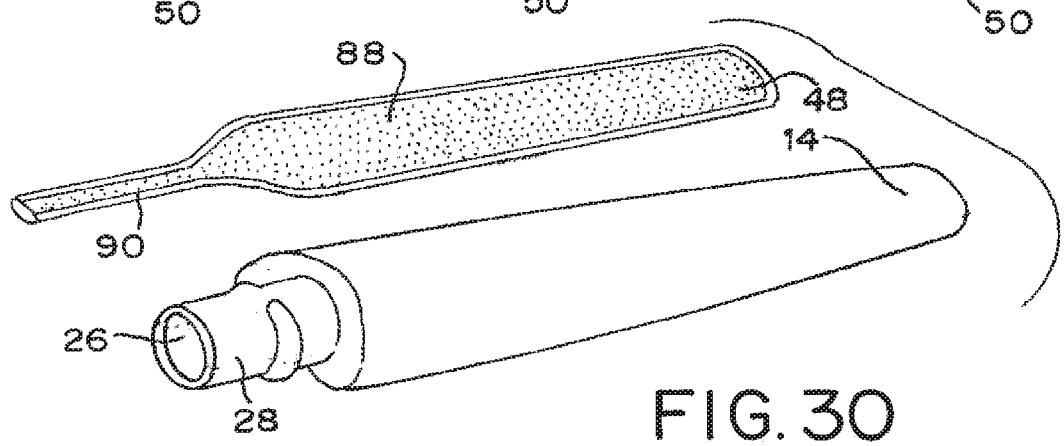

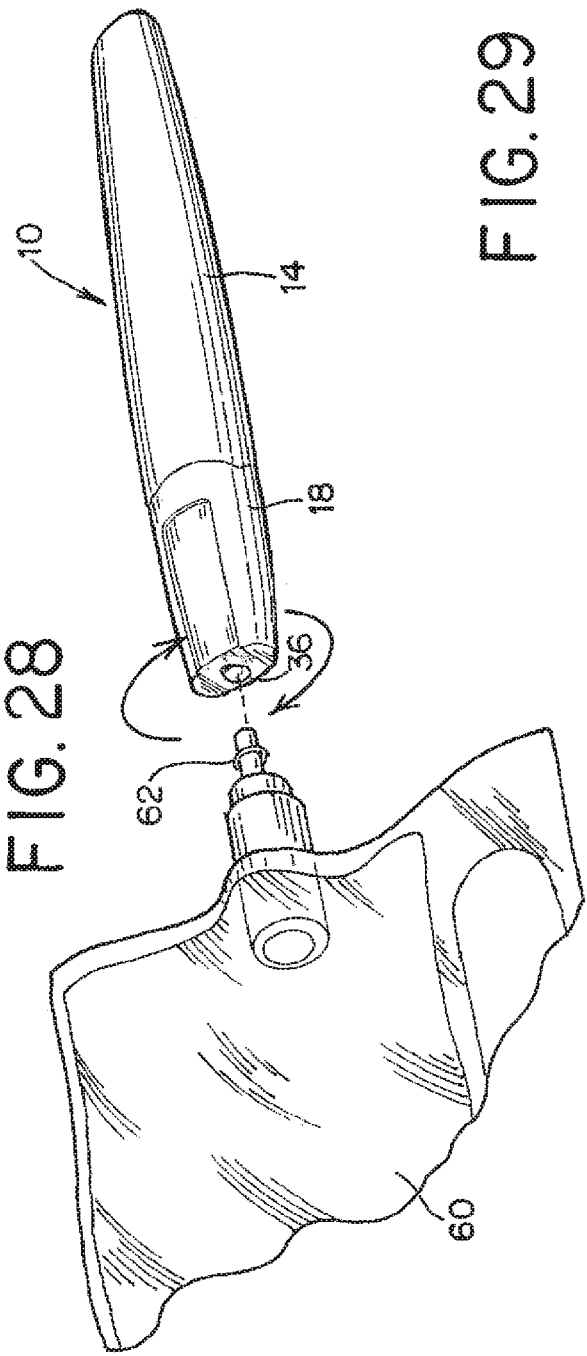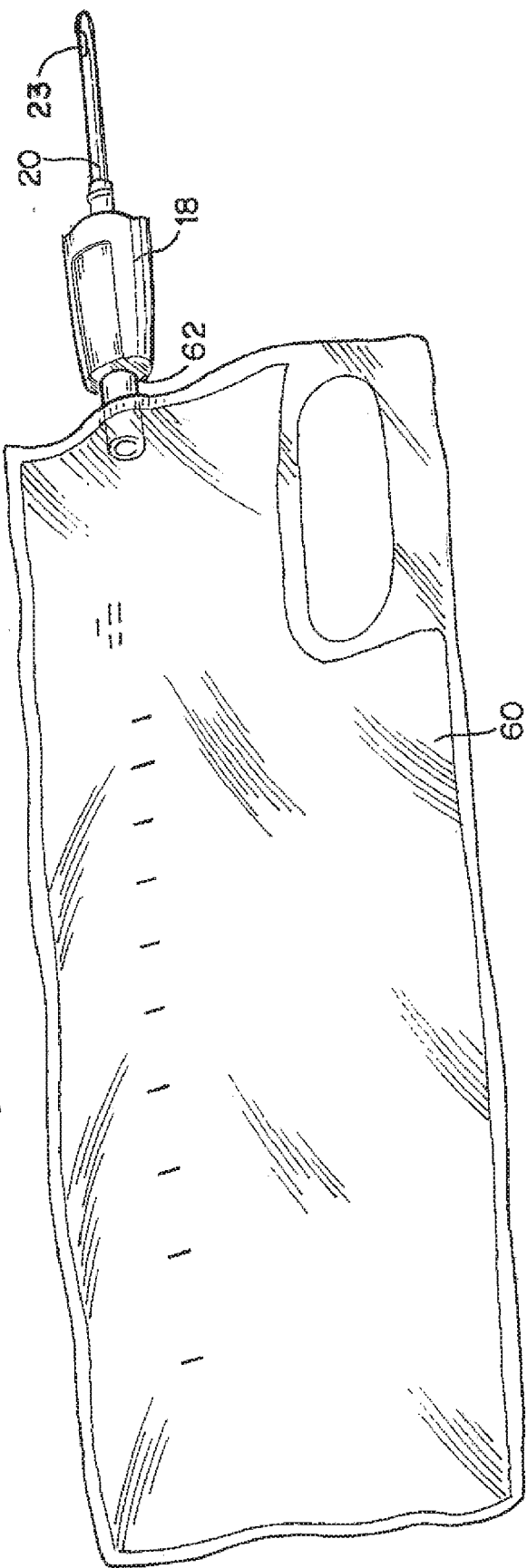

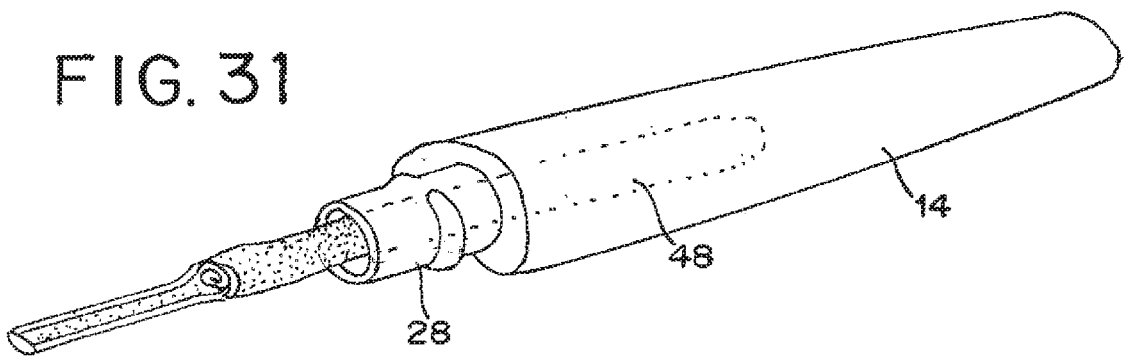
FIG. 31
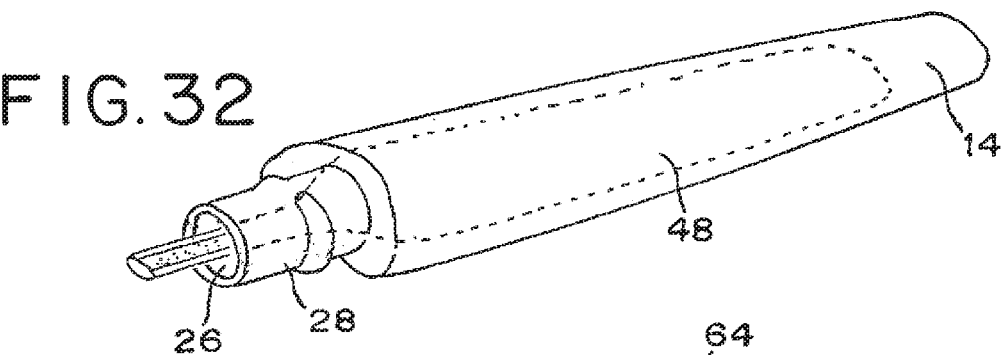
FIG. 32
FIG. 33
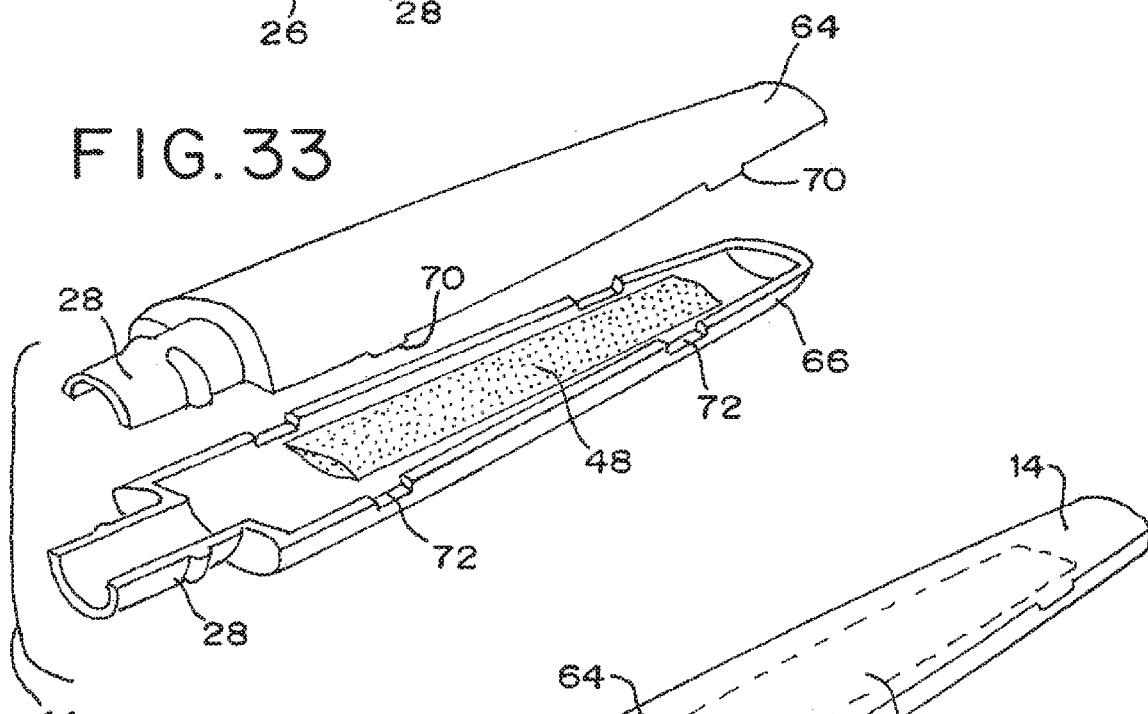
FIG. 34
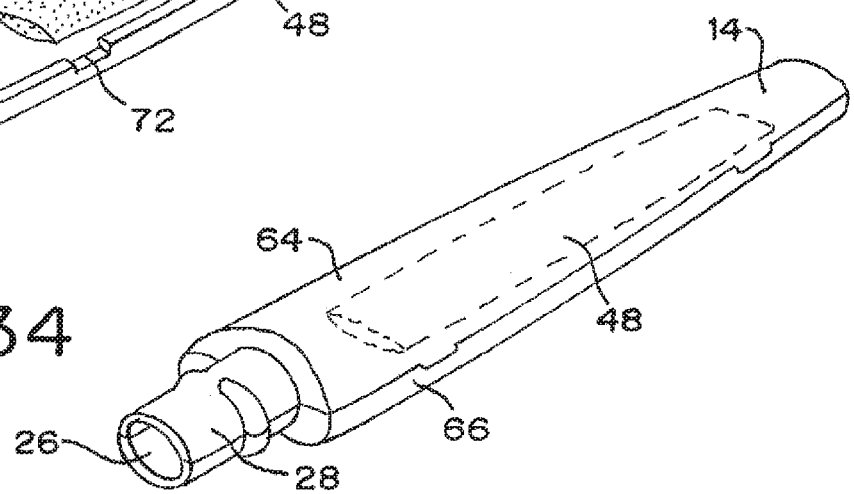

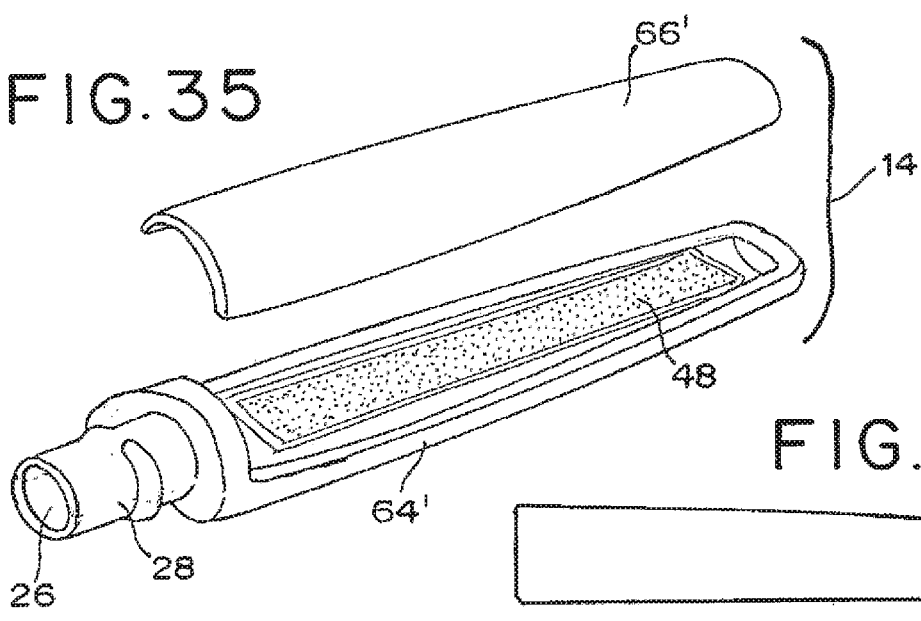
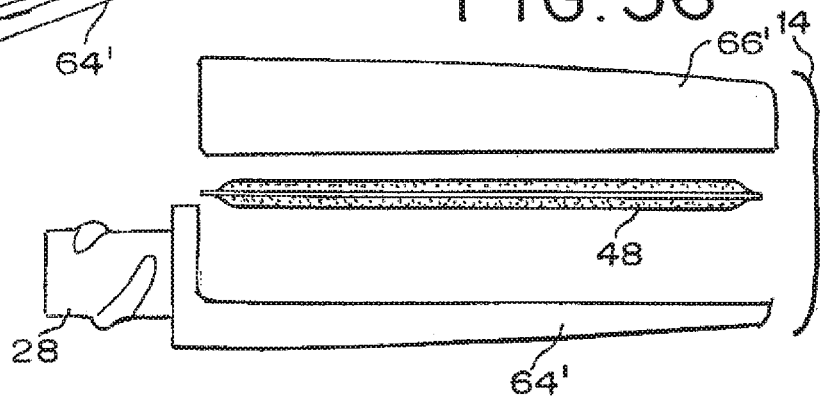
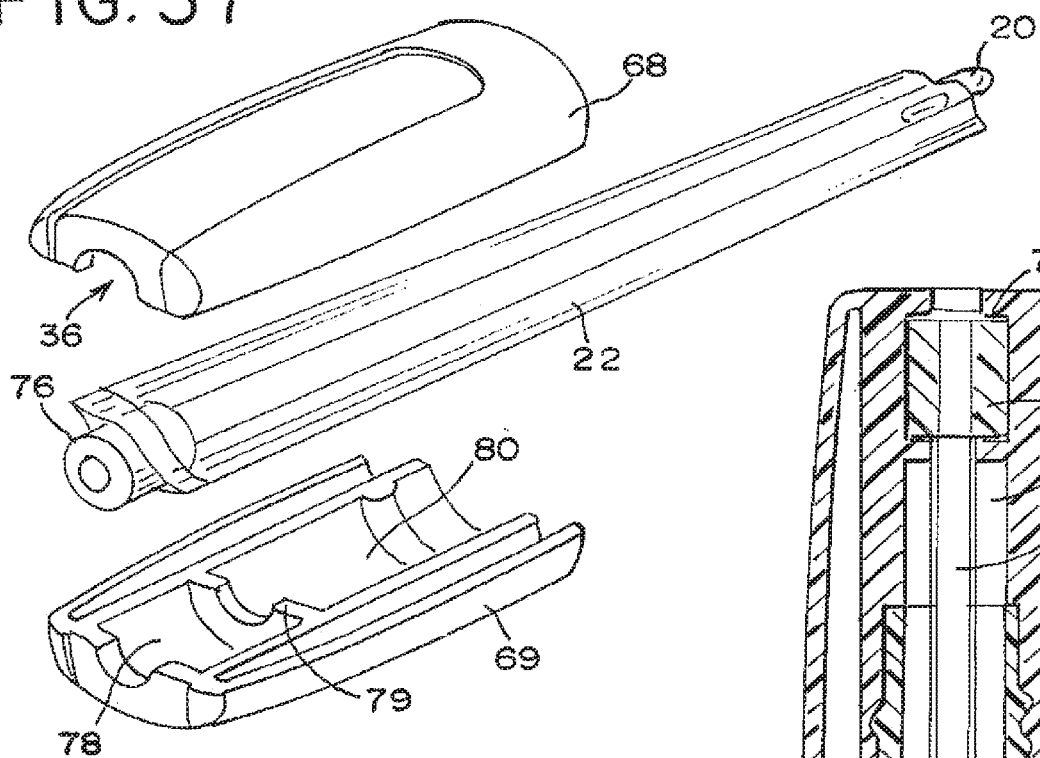
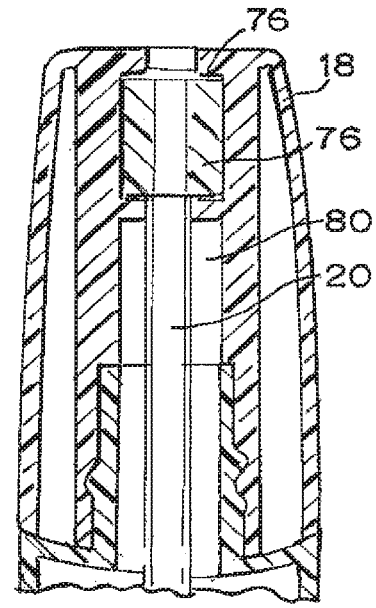

COMPACT URINARY CATHETERS AND METHODS FOR MAKING THE SAME

CROSS-REFERENCE TO RELATED APPLICATION

The present application is a divisional of U.S. patent application No. 14/775,533 which was the U.S. National Stage of PCT International Patent Application No. PCT/US2013/031643, filed Mar. 14, 2013, the contents of which are incorporated herein by reference.

FIELD OF THE DISCLOSURE

The present disclosure is directed to catheters for use in the medical field. More particularly, the present disclosure is directed to urinary catheters for use in the management of urinary incontinence. Even more particularly, the present disclosure is directed to compact intermittent urinary catheters.

BACKGROUND

Catheters are used to treat many different types of medical conditions and typically include an elongated catheter tube that is inserted into and through a passageway or lumen of the body. Urinary catheters and, in particular, intermittent urinary catheters are commonly used by individuals who suffer from certain abnormalities of the urinary system, such as urinary incontinence. With the advent of intermittent urinary catheters, individuals with problems associated with the urinary system can conveniently self-catheterize to drain the individual's bladder. Individuals who suffer from urinary incontinence will self-catheterize several times a day.

Self-catheterization involves removing the catheter assembly from its package and inserting and advancing the catheter tube through the urethra. Users of intermittent catheters are often required to self-catherize outside the privacy of the home, such as in public restrooms. Thus, for these and other reasons, it is desirable that intermittent catheters are provided in discrete packaging that is easy to open, compact and portable, and easy to dispose.

SUMMARY

In one aspect, the present disclosure is directed to a catheter assembly. The catheter assembly includes a catheter sub-assembly that has a gripping member and a catheter tube carried by the gripping member. The catheter tube defines a flow path and the gripping member has a distal end with an aperture in the distal end that communicates with the flow path of the catheter tube. The catheter assembly further includes a receiver for receiving at least a portion of the catheter tube. The receiver includes an elongated body and an outer surface and an inner surface defining an interior chamber.

In another aspect, the present disclosure is directed to a catheter assembly including a receiver and a gripping member where the receiver and gripping member when assembled define an outer, elongated housing. The housing has first and second opposed ends and a longitudinal central axis between the ends. The housing has a non-circular profile about the central axis. The catheter tube is carried by the gripping member.

In a further aspect, the present disclosure is directed to a catheter sub-assembly. The catheter sub-assembly includes a gripping member and a catheter tube carried by and attached to the gripping member. The catheter assembly has a central longitudinal axis. The catheter tube has a proximal end and distal end defining a flow path between the ends, and the gripping member includes an outer gripping surface and an aperture in the outer gripping surface in flow communication with the flow path of the catheter tube.

In a more specific aspect, the catheter assemblies and sub-assemblies disclosed herein may include a hydration element disposed within the interior chamber of the receiver. In a further more specific aspect, the hydration chamber may be a sachet that is liquid impermeable and vapor permeable.

In yet another more specific aspect, the catheter assemblies and sub-assemblies disclosed herein may include a security tab placed over the aperture in the distal end of the gripping member.

In a further more specific aspect, the security tab may also be part of a larger tamper-evidencing band that seals the junction of the receiver and gripping member.

In yet another specific aspect, the catheter and catheter sub-assemblies disclosed herein may include a full-length or partial sleeve disposed over the catheter tube of the catheter sub-assembly.

In yet another specific aspect, the catheter and catheter sub-assemblies of the present disclosure may include a notch at the proximal end of the gripping member for receiving and maintaining the catheter tube in an orientation that is angled from the central longitudinal axis.

In a further aspect, the present disclosure is directed to a method of making a catheter assembly that includes a receiver and a catheter sub-assembly. The receiver has non-circular outer housing portion defining an interior chamber and including a receiver port, while the catheter sub-assembly includes a gripping member having a non-circular outer housing and a catheter tube attached thereto. The method includes forming at least a portion of the receiver, forming the gripping member, attaching one end of the catheter tube to the gripping member, and introducing a free end of the catheter into the receiver. A security band may be applied to the juncture of the receiver and the catheter sub-assembly.

In a more specific aspect, the catheter assembly may be formed by forming a first portion of the receiver and separately forming a second portion of the receiver housing.

In a more specific aspect of the method of making the catheter assembly, the method may include introducing a hydration element into the receiver. The receiver may be attached to a wall of the interior chamber or simply placed within the interior chamber.

BRIEF DESCRIPTION OF THE DRAWINGS

FIG. 1 is a perspective view of the catheter assembly housing of the present disclosure;

FIG. 2 is an exploded view of the catheter assembly of the present disclosure showing the receiver and catheter sub-assembly.

FIG. 3 is a distal end view of the catheter assembly housing with the protective tab disposed over the aperture;

FIG. 4 is a distal end view of the catheter assembly housing of the present disclosure with the protective tab removed;

FIG. 5A is a cross-sectional side view of the catheter assembly of the present disclosure in its assembled state;

FIG. 5B is a cross-sectional side view of the catheter assembly of the present disclosure showing the catheter sub-assembly being removed from the receiver;

FIG. 5C is a cross-sectional side view showing the different components that may make up one embodiment of the catheter assembly of the present disclosure;

FIG. 6 is a cross-sectional side view of the catheter sub-assembly of FIG. 5A with a protective sleeve over the catheter tube;

FIG. 7 is a cross-sectional side view of the catheter sub-assembly of FIG. 6 showing the sleeve being retracted and the catheter tube exposed;

FIG. 12 is a perspective view of the catheter sub-assembly withdrawn from the receiver;

FIG. 13 is a side view showing the catheter tube of the catheter assembly in an upstanding orientation;

FIG. 14 is cross-sectional side view of the catheter assembly of FIG. 13 with the catheter tube in varying angled orientations;

FIG. 15 illustrates the opening of the catheter assembly of the present disclosure;

FIG. 16 is a partial end view in perspective with the protective sealing tab disposed over the aperture in the distal end;

FIG. 17 shows the catheter sub-assembly of the present disclosure grasped by a user;

FIG. 18 illustrates the removal of the protective sealing tab from the catheter sub-assembly of the present disclosure;

FIG. 19 shows another embodiment of a sealing tab/tamper evidencing band of the present disclosure;

FIG. 20 shows a step in the sequence of opening the catheter assembly by removing the tamper evidencing band;

FIG. 21 shows a further step of the opening sequence showing the removal of the tamper evidencing tab;

FIG. 22 is a partial perspective view of the receiver distal end with a portion cut away to show the hydration element disposed therein;

FIG. 23 is a cross-sectional partial view of the distal end portion of the receiver with part of a catheter tube and part of the hydration element disposed therein;

FIG. 24 is another cross-sectional side view of the end of the distal end of the receiver showing the catheter tube and the hydration element secured at the distal end of the receiver;

FIG. 25 is a partial perspective view of the distal end with a portion cut away to show the hydration element being disposed therein;

FIG. 26 is a cross-sectional side view of the distal end portion of the receiver with the catheter tube and the hydration element disposed therein;

FIG. 27 shows is a cross-sectional view of the distal end portion of the receiver with the hydration element secured at the distal end of the receiver;

FIG. 28 is a partial perspective view of a container being attached to the distal end of the catheter assembly of the present disclosure;

FIG. 29 is a perspective view of the container attached to the distal end of the catheter sub-assembly;

FIG. 30 is a perspective view of a one-piece receiver and a hydration element;

FIG. 31 is a perspective view showing the receiver of FIG. 30 with the hydration element being introduced into the receiver;

FIG. 32 is a perspective view of the receiver of FIG. 30 with the hydration element fully inserted into the receiver;

FIG. 33 is a perspective view of a method of assembling a receiver formed from two parts;

FIG. 34 is a perspective view of the receiver of FIG. 33 in its assembled state;

FIG. 35 is a perspective view of an alternative embodiment of receiver formed from two parts being assembled;

FIG. 36 is a side view of the receiver of FIG. 35;

FIG. 37 is a perspective view of one embodiment of the catheter sub-assembly with the gripper and catheter tube being assembled;

FIG. 38 is a cross-sectional side view of the gripping member of FIG. 37 with the catheter tube seated therein;

DESCRIPTION OF THE ILLUSTRATED EMBODIMENTS

Figure 8:
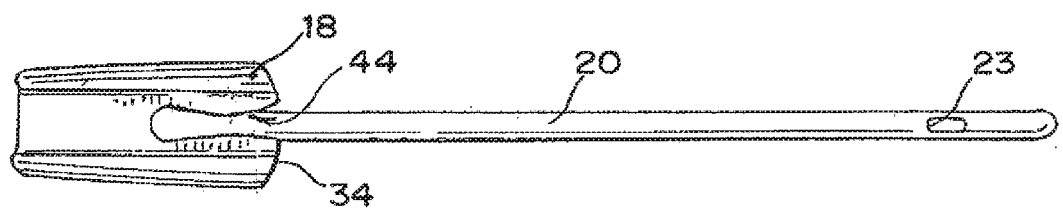
FIG. 8 is a side view of a catheter sub-assembly without a protective sleeve.
Figure 9:
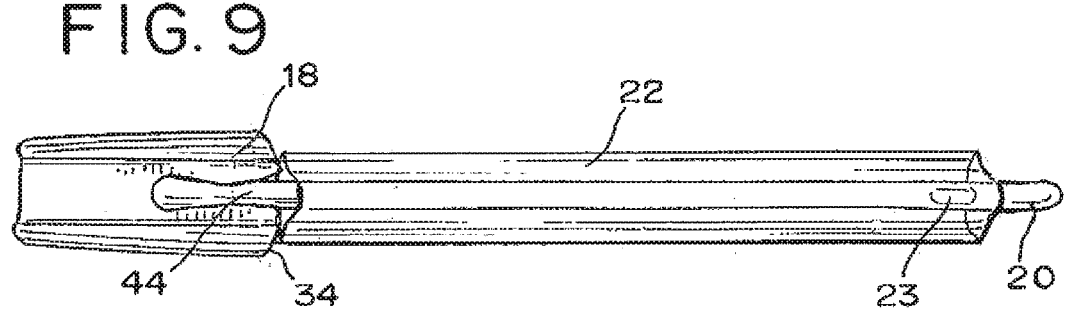
FIG. 9 is a view of the catheter sub-assembly of the present disclosure with a full-length sleeve disposed over the catheter tube.
Figure 10:
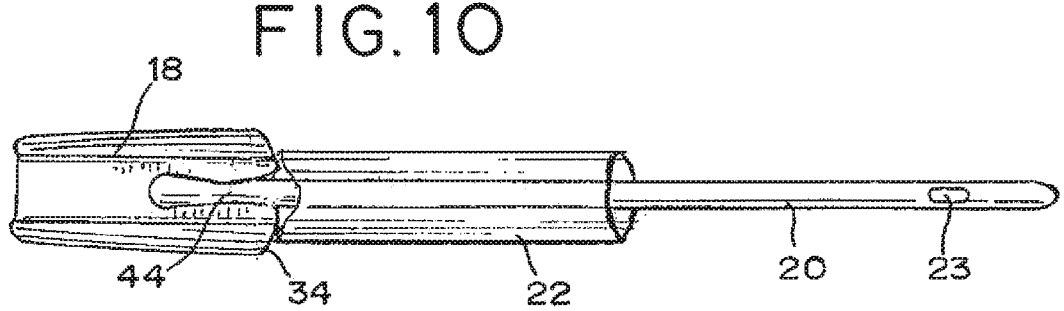
FIG. 10 is a side view of the catheter sub-assembly of the present disclosure with a partial length sleeve disposed over the catheter tube.

The embodiments disclosed herein are for the purposes of providing a description of the present subject matter. The catheter assemblies, catheter sub-assemblies, methods of use and methods of manufacture disclosed herein may be embodied in various other forms and combinations not specifically shown in detail or illustrated in any one figure. Therefore, specific embodiments are not to be interpreted as limiting and the features disclosed and illustrated are not to be interpreted as limited to any one specific embodiment described or illustrated.

FIG. 1 illustrates a catheter assembly 10 in accordance with the present disclosure. Catheter assembly 10 includes receiver 14 and catheter sub-assembly 16 that are provided in an assembled form and define an outer elongated housing 12. Catheter sub-assembly 16, in turn, includes a gripping member 18 and a catheter tube 20 carried by the gripping member 18, as shown in FIG. 2. When assembled, outer elongated housing 12 has a top surface 15a and bottom surface 15b and further includes proximal and distal ends 13a and 13b, respectively.

The terms "distal" and "proximal" are used throughout this disclosure. When used in the context of the catheter tube that is inserted into the body of the user, the term "proximal" is used to refer to that end or portion of the catheter tube that during use is closer in proximity to the user's body and/or initially enters the user's body upon insertion. The term "distal" is used to refer to an end or portion of the catheter tube that is opposite the proximal end or portion and is typically further away from the user's body. For the sake of consistency, when the terms "distal" and "proximal" are used in the context of a housing or member that receives or carries the catheter tube such as the receiver and gripping member, which are not intended for introduction into the user's body, a proximal end or proximal portion is that end or portion closer to the proximal end of the catheter tube when the catheter tube is housed or carried by such housing or member, while the distal end or portion is located opposite to such proximal end or portion.

As shown in FIGS. 1 and 2, housing 12 of catheter assembly 10 is preferably compact and portable, i.e., having a size that can, for example, be easily carried in a handbag or purse. Catheter assembly 10 and, in particular, housing 12 preferably has a longitudinal dimension sufficient to house a catheter tube 20 intended for use by a user. Female catheter tubes 20 are typically shorter in length than male catheters and have a length of approximately 100-110 mm. Housing 12 may have any shape or exterior profile that allows for easy handling by the user and is not readily identifiable as a medical product. Thus, in one embodiment, housing 12 of catheter assembly 10 has a non-circular profile or shape about the central longitudinal axis 15. More particularly, as shown in FIGS. 1-5, housing 12 of catheter assembly 10 has a generally elliptical shape or end profile about central axis 15. Housing 12 of FIGS. 1-5 is referred to as generally elliptical in the sense that it may not be a perfect ellipse but may have a top surface 15a and bottom surface 15b that are slightly flattened and side surfaces 15c and 15d that may be slightly less arcuate than a true ellipse or oval. The slightly flattened top and bottom surfaces 15a and 15b allow for a larger gripping area for grasping by a user. Of course, catheter assembly 10 of the present disclosure may be provided in other shapes that are preferably, but not exclusively non-circular. As further shown in the Figures, housing 12 may have a uniform and substantially symmetrical shape about the longitudinal axis 15 and may be free of any sharp corners and edges. Side surfaces 15c and 15d of housing 12 may be curved and of a shorter width than the top and bottom surfaces 15a and 15b, thereby providing catheter assembly 10 with a slender profile when viewed from the side. Also, when viewed from the side, housing 12 of catheter assembly 10 may include a diminishing taper toward housing ends 13a and 13b, as shown in FIG. 2.

Housing 12 is preferably made of a light-weight, substantially rigid polymeric material. Preferably, the polymeric material is a relatively rigid material that protects the contents of the catheter assembly 10. In addition, it is preferable that the polymeric material of housing 12 be non-transparent and opaque, such that the contents of housing 12 cannot be easily identified. Polymeric materials that are suitable for use in housing 12 include polycarbonate, Nylon, ABS and polyethylene. The surface of housing 12 should be reliably gripable and not slippery to the touch. Thus, at least a portion of housing 12 may be textured or roughened to enhance gripping by the user. In addition to being textured or roughened, at least gripping member 18 may further include gripping elements which may be provided by raised areas on the surface of housing 12, such as embossed lettering or the like.

As discussed above, catheter assembly 10 and, in particular, housing 12 may include a relatively wider top and bottom surfaces 15a and 15b, thereby providing the user with a wider surface area for grasping and twisting by the user during the opening sequence. As shown in FIGS. 5A-C, catheter assembly 10 is preferably made of multiple parts, including at least receiver 14 and catheter sub-assembly 8. Receiver 14 is elongated, and as discussed above, includes top and bottom exterior surfaces 15a and 15b, which together with the side surfaces 15c, 15d define and interior chamber within receiver 14. As discussed in greater detail below, receiver 14 may be of one-piece construction or multi-part construction. Receiver 14 includes a closed proximal end 14a and a distal end 14b.

In another embodiment, housing 12 may include three molded parts joined together, as shown in FIG. 5C. In the three-part embodiment, as shown in FIG. 5C, housing 12 may include receiver 14, gripping member 18 and threaded stopper 19. Stopper 19 provides the threaded neck 28 of receiver port 26. Threaded stopper 19 may be attached to the distal end of receiver 14 by press-fitting or other means. As shown in FIG. 5C, stopper 19 includes threaded neck 28 and at least a pair of proximally-extending prongs 19a/19b that snugly fit within and mate with the inner surfaces of the interior chamber of receiver 14. Further movement of stopper 19 is prevented by the distal edge of receiver 14. The entire catheter assembly 10 may be assembled by fitting the distal end of catheter tube 20 into the channel of gripping member 18. If a hydration element 48 (discussed in greater detail below) is included, hydration element 48 may first be introduced into the interior chamber prior to attachment of stopper 19. Stopper 19 may then be attached to receiver 14 which also secures the sachet of hydration element 48 within receiver 14. Stopper 19 may be secured to receiver 14 by any one of interference fit, adhesive bonding, ultrasonic welding or spin welding. Catheter sub-assembly 16 and receiver 14 may then be assembled.

As shown in FIG. 5C, in one embodiment, distal end 14b includes contacting surface 32, which contacts a corresponding surface of gripping member 18 when catheter assembly 10 is in its assembled state. Distal end surface 32 may be shaped in a way that is complementary to the shape of the distal end of gripping member 18. Distal end surface 32 includes an opening to allow for insertion of catheter tube 20.

As shown in the FIGS. 2 and 5A-5C, in one embodiment, distal end surface 32 includes and/or supports a receiver port 26. Receiver port defines an opening in receiver 14 that allows insertion of catheter tube 20 of catheter sub-assembly 16. Receiver port includes a neck 28 which terminates in an opening in port 26 sufficiently sized to receive a catheter tube 20 and from which catheter tube can be freely withdrawn. Neck 28 may include an engagement surface for cooperative engagement with a corresponding surface of gripping member 18. Thus, as shown in FIG. 5C, neck 28 may be threaded to allow for threaded engagement and disengagement with corresponding threads on gripping member 18. Other means of securing receiver 14 to gripping member 18 that will be known to those of skill in the art are also within the scope of this disclosure.

As indicated above and with reference to FIGS. 6-7, catheter sub-assembly 16 includes gripping member 18 and catheter tube 20 attached to and carried by gripping member 18. Catheter tube 20 includes a proximal end portion 21 and distal end portion. Preferably, catheter tube 20 is carried by and secured to gripping member 18 at the distal end of catheter tube 20. Catheter tube 20 defines a flow path for urine that is drained from the body of a user. Thus, catheter tube 20 includes eyelet openings 23. Urine enters through the eyelets 23 and travels down the flow path of catheter tube 20 where it can be drained into a toilet (WC) or an attached receptacle.

Catheter tube 20 may be made of a biocompatible polymeric material having sufficient stiffness that it can be easily inserted into the body of the user, yet flexible enough to avoid causing pain or discomfort to the user and to allow for movement within the urinary canal. Materials that are suitable for use as catheter tube 20 include polyvinyl pyrrolidone (PVP), polyamide, polyanhydride, polyether, poly (ether imide), poly(ester imide), polyvinyl alcohol, polyvinyl chloride, polycarbonate, poly($\varepsilon$-caprolactone)

with polymethylvinylsiloxane, poly(ethylene-co-(vinylacetate)) with dicumylperoxide, poly(D-lactide), poly(L-lactide), poly(DL-lactide) and poly(glycolide-co-(ε-caprolactone))-segments, multiblock copolyesters from poly(ε-caprolactone) and PEG and chain extender based on cinnamic acid groups, poly(ε-caprolactone) dimethacrylate and n-butyl acrylate, oligo(ε-caprolactone) diols, oligo (p-dioxanone) diols and diisocyanate, linear density polyethylene, linear low density polyethylene, high density polyethylene, and polypropylene. Catheter tube 20 may also be entirely made of a hydrophilic material or a material that has been made hydrophilic. Catheter tube may also include a hydrophilic coating on at least a portion of outer surface thereof, which when contacted by an aqueous, partially aqueous, or non-aqueous liquid enhances the lubricity (and reduces the co-efficient of friction) of catheter tube 20. Catheter tubes that are activated by agents to make the catheter tube 20 more lubricious are known and sold in products under the trademarks VaPro™ and VaPro™ Plus, sold and distributed by Hollister Inc. of Libertyville, Ill. Additional details of such hydrophilic catheters and activation thereof are described in U.S. Pat. No. 8,051,981, which is incorporated herein by reference. Alternatively, catheter tube 20 may be lubricated by providing a friction-reducing material such as a gel within a reservoir of introducer tip 46 (shown in FIG. 11 and further described below), which coats catheter tube 20 as catheter tube passes through introducer tip 46. Catheter assemblies that include a gel reservoir in a protective introducer tip are sold in products under the trademarks Advance™ and Advance™ Plus, also distributed by Hollister Inc. of Libertyville, Ill..

Figure 11:
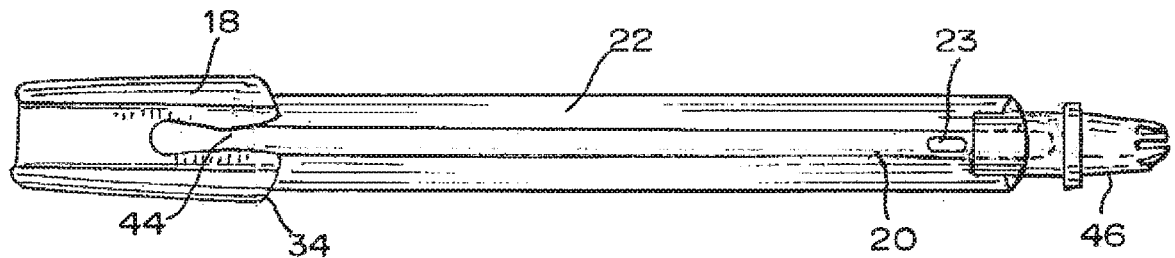
FIG. 11 is a side view of the catheter sub-assembly of the present disclosure showing a full-length sleeve disposed over the catheter tube and a introducer tip located at the distal end tip of the catheter tube.

As shown in FIGS. 2, 6-7 and 9-11, catheter tube 20 may optionally be provided with a partial or substantially full-length sleeve 22 over the outer surface of catheter tube 20. Sleeve 22 may be made of a flexible, relatively thin polymeric film material that allows the user to grasp catheter tube 20 through sleeve 22 and thereby avoid direct contact with catheter tube 20 and the possibility of contamination of catheter tube 20. For example, in use, the user grasps and manipulates catheter tube 20 through sleeve 22, advancing catheter tube 20 into the urethra while folding or bunching sleeve 22 at the distal end portion 21 of catheter tube 20, as seen in FIG. 7. "No-touch" sleeve 22 is preferably made of a material that is capable of being folded onto itself or bunched during insertion of catheter tube 20. Polymeric film materials suitable for use as sleeve 22 include (but are not limited to) polyethylene, plasticized PVC, polypropylene, polyurethane or elastomeric gels. With reference to FIG. 11, catheter tube 20 may further include introducer tip 46 placed over the catheter tip at proximal end portion 21 Introducer tip 46 is used to assist in positioning of the proximal end of catheter tube 20 during introduction into the urethra of the user, and to protect the proximal end of the catheter tube 20 from contamination by bacteria in the distal urethra.

Referring to FIGS. 12-14, catheter tube 20 extends from gripping member 18 and is generally oriented along and coincident with central longitudinal axis 15. However, during introduction (or withdrawal) of catheter tube 20, users may wish to adjust the orientation of catheter tube 20 for positioning over a receptacle and/or for physical comfort. Thus, in accordance with the present disclosure, catheter tube 20 may be adjusted and maintained at an angle to central longitudinal axis 15. In one embodiment shown in FIGS. 13-14, the position of catheter tube 20 may be angularly adjusted relative to the central longitudinal axis 15 by a desired angle α. Catheter tube 20 may be tilted and bent away from the central longitudinal axis 15 at angles up to approximately 90°, if desired, but more typically on the order of 45° or less.

In that regard, as further seen in the FIGS. 12-14, gripping member 14 may include a notch 44 positioned at or near proximal end surface 34 of gripping member 14. When catheter tube 20 is adjusted to the desired angle relative to the central longitudinal axis 15, as described above, notch 44 provides a retainer for maintaining catheter 20 in such angled position. Notch 44 may be keyhole-shaped and include a narrow channel 44a that opens to a wider window 44b (as shown in FIG. 12) sized to comfortably receive catheter tube 20 without squeezing, pinching or kinking of the catheter tube 20. Thus, as shown in FIG. 14, catheter tube 20 may be disposed in a relatively vertical orientation (i.e., bent at an approximately 90° angle) when held within window 44b or a more angled orientation (less than approximately 90°) when held within channel 44a.

In addition, to carrying catheter tube 20 and providing a gripping surface for the user, gripping member 18 also provides a closure for receiver 14 of housing 12. As discussed above, gripping member 18 includes a proximal end or surface 34 that has a profile or shape that is complementary to the profile or shape of receiver distal end surface 32, previously discussed, when receiver 14 and catheter subassembly 16 are brought together in an assembled state. Thus, as shown in FIG. 2, if proximal end surface 32 of receiver is concave, distal end of gripping member 18 will typically be convex. Surfaces 32 and 34 may have other shapes or profiles that are likewise complementary, including non-curves, generally flat surface as shown in FIG. 5C. When the end surfaces 32 and 34 are in contact and receiver 14 and gripping member 18 are assembled, separation line 42 may be visible (FIG. 1).

In an embodiment, gripping member 18 also includes aperture 36 in the distal end 19b of gripping member 18. Aperture 36 is in flow communication with the flow path of catheter tube 20 and provides an outlet for urine that is drained from the bladder of the user. In one embodiment shown in FIGS. 5A-5C, aperture 36 communicates with flow path of catheter tube 20 through, for example, channel 37 located at the distal end of gripping member 18. Channel 37 may include a surface that is suited for engagement by an attachment member of a urine collection receptacle (discussed in more detail below). Thus, in one embodiment, surface 39 of channel 37 may be threaded. In another embodiment, a corresponding attachment member of the urine collection receptacle may provide a surface adapted for friction-securement with aperture 36.

Prior to use, aperture 36 may be sealed from the outside environment to protect the contents of the catheter assembly 10 from ingress of airborne bacteria or microorganisms through aperture 36, and also to prevent premature urine flow. Thus, gripping member 18 preferably includes a removable tab 38 or other sealing element over aperture 36, shown in FIGS. 15-18. In one embodiment, sealing tab 38 may be a tape having an adhesive on at least a portion of the underside that adheres to the outer surface of housing 12. Tab 38 is applied onto top surface 15a and/or bottom surface 15b and over distal end 19b of gripping member 18. Tab 38 may include a wider region 38a that provides an enlarged grasping surface for the user and that narrows to a narrower strip portion 38b. Tab 38 preferably is made of a foil or other oxygen or moisture barrier material that can be heat sealed and/or otherwise adhered to the surface of gripping member 18.

Tab 38 may extend into receiver 14 across separation line 42 as shown in FIG. 16. Relative twisting (e.g., 180°) of receiver 14 and gripping member 18 breaks the tab along separation line 42, as shown in FIG. 15. In that regard, tab 38 may also function as a tamper evidencing band. Gripping member 18 may further include a recess or depression 41 to accommodate and/or receive a portion of tab 38. Recess 41 may be located on top or bottom surfaces 15a and/or 15b of gripping member 18, as shown in FIG. 18. Recess 41 may extend across separation line 42 into receiver 14, as necessary. Recess 41 provides room for the user to grasp an end of tab 38 to begin the unsealing process. In use, sealing tab 38 may remain over aperture 36 until catheter tube 20 has been introduced into the urethra and gripping member 18 is comfortably positioned over the urine receptacle (e.g., toilet, WC). Where a container or receptacle is attached to gripping member 18, tab 38 must first be removed, container attached and catheter tube 20 then introduced in the urethra.

In another embodiment, tab 38 may be part of a larger and longer tamper band 40, as shown in FIGS. 19-21. Tamper band 40 may be shaped and configured to allow for sealing of the catheter assembly along separation line 42, while also acting as a sealing member over aperture 36. As shown in FIGS. 19-21, tamper band 40 may be wrapped around housing 12 at separation line 42 and include a portion that is generally perpendicular to the band section about separation line 42 that extends over gripping member 18 and, more specifically, over aperture 36. FIGS. 19-21 show the unwinding sequence of such a tamper band 40, whereby the user grasps an end of the tamper band and by pulling tamper band 40 removes it from separation line 42. Continued pulling of tamper band 40 then exposes aperture 36 and makes the catheter assembly ready for use.

As discussed previously, catheters, and specifically catheter tube 20 of the type disclosed herein, are preferably made of a hydrophilic material with a coating applied to the outer surface thereof where the coating is wetted or activated by a suitable agent to make tube 20 lubricous or more lubricious and reduce the coefficient of friction to allow for easy advancement and movement through the urethra. The lubricating agent, preferably water or other aqueous solution, may be directly applied to tube 20 from liquid contained within a package or, more preferably, may be released and come into contact with tube 20 either as liquid or vapor over a period of time.

Thus, in accordance with the present disclosure and as shown in FIGS. 5A-5C, the catheter assembly described herein may include a hydration element that is used to activate catheter tube 20. Hydration element 48 may provide water or the other aqueous solution as a vapor or liquid. Hydration element may be contained within the interior chamber of receiver 14.

In one embodiment, hydration element 48 is provided as a sealed sachet or pillow 48 that includes water or other aqueous solution within it. Hydration element 48 is preferably made of a suitable material that is selected to release the hydrating agent through its walls. In addition, the hydration element may include an insert made of a material that retains water or other aqueous solution. In one embodiment, the insert may be made of calcium carbonate, while the walls of the hydration element containing the insert may be made of a polymeric material that is vapor permeable but liquid impermeable.

With reference to FIGS. 33-36, hydration element 48 may be freely placed within the interior chamber of receiver 14. Alternatively, as shown in FIGS. 23-27, hydration element 48 or a portion thereof may be secured to the inner wall defining the interior chamber of the receiver 14. In one embodiment, an elongated hydration element 48 extends along the elongated inner wall of receiver 14 and to the elongated wall along one or both edges of element 48. Alternatively, an end of hydration element 48 may be secured to the inner proximal end wall of the interior chamber of receiver 14. As shown in FIGS. 22-27, hydration element 48 may be attached at one end 48a to interior end wall of the receiver closed distal end 14a. Hydration element 48 may be attached by light spot welding or adhesive. Alternatively, as seen in FIGS. 22-27, hydration element 48 may be provided with a hole or slit 49 located at its end, which is sized to fit over retaining post 50 in receiver 14. Post 50, in turn, may be in the form of one or more upstanding prongs 52, which when bent or folded downwardly press the end of retaining element 48 and secure the end of hydration element 48 within receiver 14. Of course, other means of securing hydration element 48 may also be used.

As indicated above and shown in FIGS. 28-29, aperture 36 of gripping member 18 may serve as an outlet port for urine that has been drained from the patient. Aperture 36 may also provide an attachment point for a urine collection container 60. The urine collection container 60 may likewise have an end suited for attachment to aperture 36. For example, where gripping member 18 includes aperture 36 and a channel 37 with an internal threaded surface 39, container 60 may be provided to include a corresponding external thread or attachment member 62, as shown in FIG. 30. Attachment of container 60 to aperture 36 may also be accomplished by other means, such as a friction fit between a corresponding ring or bead on attachment member 62 capable of being press-fit in a corresponding slot of channel 37.

The individual components of receiver 14 and catheter sub-assembly 16 and more specifically gripping member 18 may be made of single and/or multi-piece construction. As discussed above, receiver 14 and gripping member 18 that define housing 12 are preferably made of rigid polymeric material. In one embodiment, receiver 14 and gripping member 18 of housing 12 may be molded. In one more particular embodiment, receiver 14 may be blow molded, providing a one-piece receiver 14, as shown in FIGS. 30-32. Alternatively, receiver 14 may be of two-part construction with each part being, for example, separately injection molded and subsequently assembled together. As shown in FIGS. 35-36, receiver 14 may be made of two injection molded parts 64 and 66. Receiver parts 64 and 66 may then be joined together in a snap-fit arrangement by providing each of the parts 64 and 66 with corresponding tabs 70 and notches 72 for interengagement. Parts 64/66 may be secured or further secured by adhesive or ultrasonic welding to provide a closed, sterile housing. The molded parts 64 and 66 may be substantially identical and/or identically sized or, as shown, in FIGS. 35-36, can be separately molded as a base 64' and lid 66'. Parts 64' and 66' may be secured to each other by tabs and notches as described above, and by adhesive or ultrasonic welding.

Similarly, as shown in FIG. 37 gripping member 18 may be made of two-piece construction, including two corresponding injection molded parts 68 and 69 each having comparable and corresponding tabs 70 and notches 72 for attachment (not shown). As with receiving member 14, the two-parts of gripping member 18 may further be secured using adhesive or ultrasonic welding.

Catheter tube 20 may be assembled with gripping member 18 in any one of several ways. As shown in FIG. 38, catheter tube 20 may be provided with a hub 76 attached at or near distal end of catheter tube 20. Hub 76 may be in the form of a cylindrical barrel or other shape. Hub 76 may also be the cylindrical portion of a pre-existing and pre-attached catheter tube funnel, as described in International Patent Publication No. WO 2012/134804, which is incorporated herein by reference. Where sleeve 22 is provided with catheter tube 20, sleeve 22 may be lightly welded or otherwise adhered to hub 76.

Figure 39:
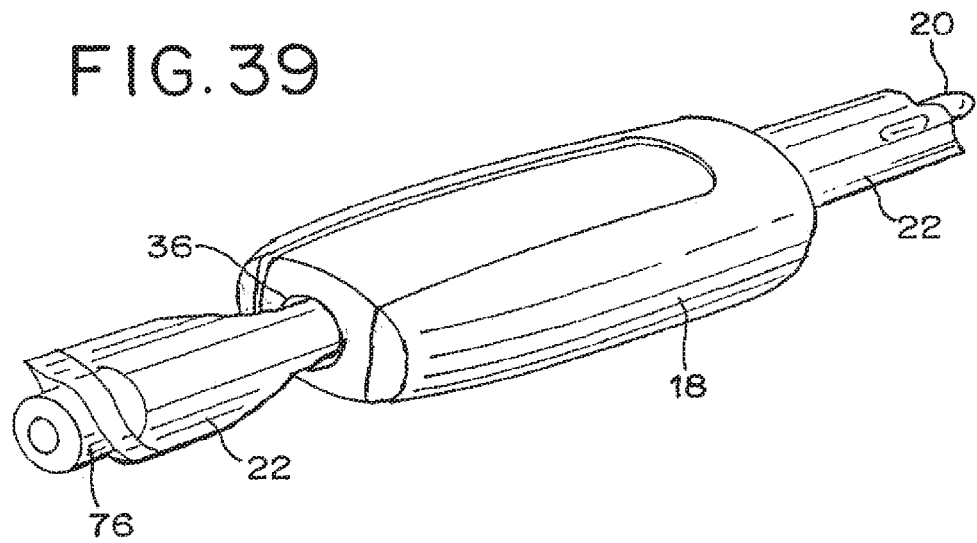
FIG. 39 is a perspective view showing one method by which catheter tube may be introduced into the gripping member.
Figure 40:
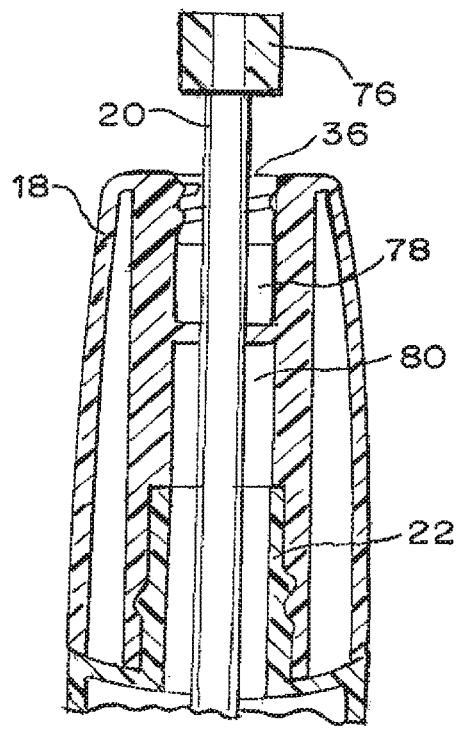
FIG. 40 is a cross-sectional side view showing the step of introducing the catheter tube into the gripping member as shown in FIG. 38.
Figure 41:
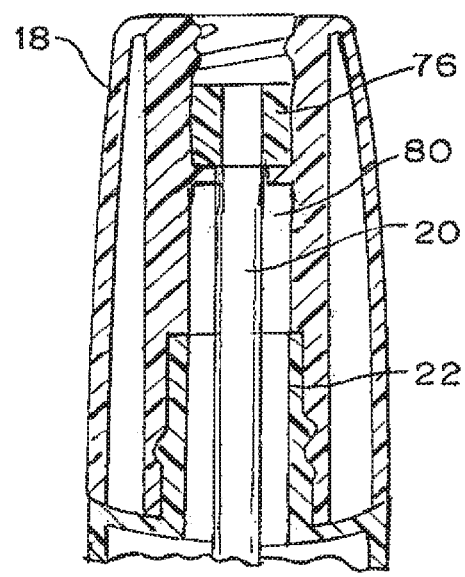
FIG. 41 is a cross-sectional side view showing the catheter tube fully seated and installed and assembled with the gripping member.

Gripping member 18 may be molded or otherwise formed to include compartments 78 and 80 to receive/accommodate hub 76 and sleeve 22. Compartment 78 may be distally located and sized and adapted for receiving hub 76. In one embodiment, compartment 78 may be sized to receive hub 76 in a press-fit or snap-fit relationship. A second compartment 80 may be proximally located relative to compartment 78 and may be sized to accommodate sleeve 22 as sleeve is folded and/or bunched up during introduction of catheter tube 20. As shown in FIG. 37, compartments 78 and 76 are separated from one another by inwardly extending wall segments 79, which prevents movement of hub beyond compartment 76. Where gripping member 18 is made of two-piece construction from separately molded parts, each half or molded portion of gripping member 18 will include a half of compartments 76 and 78. In an alternative embodiment, catheter tube 20 with hub 76 and optional sleeve 22 may simply be inserted through aperture 36, as shown in FIGS. 39-41. Catheter tube 20 with hub 76 may be pressed through aperture 36 until hub is seated within a corresponding compartment in an interference fit-type engagement.

With reference back to FIGS. 30-32, where receiver 14 is made of blow molded construction, hydration element 48 may also be provided in the shape of a bottle having a widened chamber 88 and container neck 90, as shown in FIG. 32. In such embodiment, hydration element 48 may be rolled or folded and introduced through the receiver port 26, as shown in FIGS. 33-34. Once inside the interior chamber of receiver 14, hydration element 48 will unroll and expand. Water or other aqueous solution used for hydration may then be introduced through the neck portion 88 of hydration element 48. Neck portion may then be sealed to prevent leakage or escape of liquid from hydration element 48.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A catheter assembly comprising:
   a) a catheter sub-assembly comprising a gripping member and a catheter tube with a proximal end and a distal end carried by said gripping member, said catheter tube defining a flow path, said gripping member having a distal end and an aperture in said distal end;
      wherein said catheter sub-assembly has a longitudinal axis coincident with said catheter tube and said aperture and said catheter tube is angularly adjustable relative to said axis; and
   b) a receiver for receiving at least a portion of said catheter tube, said receiver comprising an elongated body comprising an outer surface and an inner surface defining an interior chamber;
      wherein each of said gripping member and said receiver comprises contacting end surfaces and the gripping member contacting end surface comprises a notch sized to receive said catheter tube.

2. The catheter assembly of claim 1 wherein said receiver comprises an open distal end.

3. The catheter assembly of claim 1 wherein each of said receiver and said catheter sub-assembly include engagement surfaces for engagement of said gripping member and said catheter sub-assembly.

4. The catheter sub-assembly of claim 3 wherein said receiver comprises a distally extending neck comprising said receiver engagement surface.

5. The catheter assembly of claim 3 wherein each of said receiver and catheter sub-assembly engagement surfaces comprises threaded surfaces.

6. The catheter assembly of claim 1 wherein said gripping member and said receiver are made of molded polymeric material.

7. The catheter assembly of claim 1 wherein said gripping member provides a closure for said receiving member.

8. The catheter assembly of claim 1 wherein said contacting end surfaces include complementary profiles.

9. The catheter assembly of claim 8 wherein said contacting end surface of one of said receiver and said gripping member has a generally concave profile and said end surface of said other of said receiver and said gripping member has a generally convex profile.

10. The catheter assembly of claim 1 wherein said catheter sub-assembly includes a removable seal over said aperture.

11. The catheter assembly of claim 10 comprising a tamper band.

12. The catheter assembly of claim 11 wherein said tamper band is disposed at said contacting end surfaces of said receiver and gripping member when assembled.

13. The catheter assembly of claim 12 wherein said tamper band is continuous with said removable aperture seal.

14. The catheter assembly of claim 10 wherein said contacting end surfaces of said receiver and said gripping member when assembled define a separation line sealed by said tamper band.

15. The catheter assembly of claim 14 wherein a portion of said tamper band seals said separation line and a portion of said band seals said aperture.

16. The catheter assembly of claim 1 wherein said catheter sub-assembly further comprises a flexible sleeve disposed over at a least a portion of said catheter tube.

17. The catheter assembly of claim 16 wherein said sleeve is gas permeable.

18. The catheter assembly of claim 1 wherein said catheter sub-assembly comprises a hub associated with said catheter tube.

19. The catheter assembly of claim 18 wherein said hub is positioned at said distal end of said catheter tube.

20. The catheter assembly of claim 19 wherein said catheter tube is coaxial with said hub.

21. The catheter assembly of claim 18 wherein said gripping member comprises a compartment for receiving said hub.

22. The catheter assembly of claim 21 wherein said gripping member comprises a sleeve-collecting compartment.

23. The catheter assembly of claim 22 wherein said sleeve-collecting compartment is proximally spaced from said hub-receiving compartment.

24. The catheter assembly of claim 1 wherein said gripping member comprises a channel between a distal end of said catheter tube and said aperture.

25. The catheter assembly of claim 24 wherein said channel comprises an inner surface adapted for attachment of a container.

26. The catheter assembly of claim 25 wherein said channel inner surface is threaded.

27. The catheter assembly of claim 25 further comprising a container.

28. The catheter assembly of claim 1 further comprising a hydration element.

29. The catheter of claim 28 wherein said hydration element is contained within said interior chamber of said receiver.

30. The catheter assembly of claim 28 wherein said hydration element comprises a sachet containing a moisture-donating liquid.

31. The catheter assembly of claim 30 wherein said moisture-donating liquid comprises liquid water.

32. The catheter assembly of claim 28 wherein said hydration element is made of a material that is liquid impermeable and vapor permeable.

33. The catheter assembly of claim 28 wherein said hydration element is secured within said receiver interior chamber.

34. The catheter assembly of claim 28 wherein said hydration element is secured to said inner surface of said receiver.

35. The catheter assembly of claim 28 wherein said hydrating element is secured to said a closed distal end of said receiver.

36. The catheter assembly of claim 1 wherein said catheter sub-assembly includes an introducer tip at the proximal end of the catheter tube.

37. The catheter assembly of claim 1 wherein said notch has a key-hole shaped profile comprising a generally circular portion and a non-circular portion.

\* \* \* \* \*